(12) United States Patent
Ouellette (10) Patent No.: US 6,844,540 B2
(45) Date of Patent: Jan. 18, 2005

(54) CONVEYOR SENSOR AND CONVEYOR PATH RESTRICTION FOR CONVEYED OBJECTS HAVING TRIANGULAR CROSS SECTIONS

(75) Inventor: Joseph F. Ouellette, Glendale, MO (US)

(73) Assignee: Ouellette Machinery Systems, Inc., Fenton, MO (US)

( * ) Notice: Subject to any disclaimer, the term of this patent is extended or adjusted under 35 U.S.C. 154(b) by 437 days.

(21) Appl. No.: 09/861,827

(22) Filed: May 21, 2001

(65) Prior Publication Data

US 2002/0171035 A1 Nov. 21, 2002

(51) Int. Cl.[7] .............................................. H01J 40/14

(52) U.S. Cl. .............................. 250/223 B; 250/223 R (58) Field of Search ........................ 250/223 B, 223 R; 209/521–522; 356/239.4

(56) References Cited

U.S. PATENT DOCUMENTS

| | | | |
|---|---|---|---|
| 3,724,639 A | | 4/1973 | Hara |
| 3,797,195 A | * | 3/1974 | Brink et al. ................... 53/471 |
| 3,990,566 A | | 11/1976 | Nordqvist |
| 4,132,305 A | | 1/1979 | Mastak |
| 4,256,957 A | * | 3/1981 | Ford et al. ............... 250/223 B |
| 4,959,538 A | * | 9/1990 | Swart ...................... 250/223 B |
| 5,141,110 A | * | 8/1992 | Trischan et al. ............ 209/524 |
| 5,224,330 A | | 7/1993 | Stahlecker |
| 5,311,979 A | * | 5/1994 | Risley et al. ............... 198/453 |
| 5,368,151 A | | 11/1994 | Klenk |
| 5,895,911 A | * | 4/1999 | Giometti et al. ......... 250/223 B |
| 5,896,195 A | * | 4/1999 | Juvinall et al. .......... 250/223 B |
| 6,448,549 B1 | * | 9/2002 | Safaee-Rad ............. 250/223 B |

* cited by examiner

Primary Examiner—Zandra V. Smith
(74) Attorney, Agent, or Firm—Thompson Coburn LLP (57) ABSTRACT

A conveying system includes a photoelectric sensor and a gate where the sensor senses objects having triangular cross sections that are conveyed past the sensor by the conveyor system and the gate is configured to close across the conveyor path and hold back the objects having triangular shaped cross sections.

24 Claims, 7 Drawing Sheets

CONVEYOR SENSOR AND CONVEYOR PATH RESTRICTION FOR CONVEYED OBJECTS HAVING TRIANGULAR CROSS SECTIONS

This application is related to application Ser. No. 09/862,047, filed May 21, 2001 incorporated herein by reference.

BACKGROUND OF THE INVENTION

(1) Field of the Invention

The present invention pertains to a photoelectric sensor and a restriction in a conveyor path that are parts of a conveying system. The sensor senses objects having triangular cross sections that are conveyed past the sensor by the conveyor system and the conveyor path restriction positions the conveyed triangular shaped objects where they can be engaged by a hold back gate.

(2) Description of the Related Art

The conveyor sensor and conveyor path restriction of the invention may be employed in any part of a conveyor system that conveys objects having irregular shaped cross sections to sense objects conveyed by the conveyor system and position the objects in the conveyor path where they can be engaged by a hold back gate to hold back objects conveyed by the conveyor system, but in the preferred embodiment of the invention the sensor and restriction are employed on an infeed conveyor that supplies several rows of objects having triangular shaped cross sections to a row former of a conveyor system.

Row formers are typically used in conveying systems that convey objects, for example light-weight blow molded plastic containers, in one or more single file streams of the objects from one station of the conveying system to another, for example, from a blow molding station where the containers are formed to a downstream palletizing station where the containers are arranged on pallets. The row former receives the objects from the one or more single file streams of objects conveyed by an infeed conveyor, arranges predetermined numbers of the objects in rows, and positions the rows side-by-side on a row accumulating table forming two dimensional arrays of the objects. Each two dimensional array of the objects is then typically swept as a layer of objects onto a pallet, becoming one layer of objects among the stacked layers of objects loaded onto the pallet.

The typical infeed conveyor is comprised of one or more conveyor belts on which numbers of the objects are conveyed in single file lines to the row former. The typical row former receives the streams of objects conveyed by the infeed conveyor belts and arranges numbers of objects in rows and then positions sequentially arranged rows of the objects side-by-side on the accumulating table of the conveyor system, forming a two dimensional array of the objects that are later palletized.

The row former includes one or more pairs of spaced, parallel arms or pusher bars that define one or more row forming slots between the arms for each line of objects conveyed by the infeed conveyor. The arms are positioned above the infeed conveyor where the slots between the arms receive numbers of objects from the streams of objects conveyed by the infeed conveyor. With the desired numbers of objects filling the slots of the row former, the conveyed streams of objects are held back by closing hold back gates of the infeed conveyor and the row former, with the arranged rows of objects, moves in a direction perpendicular to the rows a short distance across the infeed conveyor and onto a surface of the accumulating table. The arms of the row former then stop and move upwardly from the accumulating table, leaving the numbers of objects in the first arranged rows of objects on the table surface.

The row former arms are then moved in the opposite direction back across the accumulating table surface to their positions in line with the infeed conveyor conveying the streams of objects to the row former. The arms are then moved downwardly aligning the slots between the pairs of arms again with the infeed conveyor conveying the streams of objects to the row former. The gates of the infeed conveyor are opened and the slots between the row former arms are again filled with predetermined numbers of objects, following which the gates of the infeed conveyor are closed. The movement of the row former arms described above is then repeated, leaving numbers of objects in the second arranged rows on the accumulating table surface. This movement of the row former is repeated in forming a two dimensional array of the objects on the accumulating table surface.

Prior art infeed conveyors and row formers have worked well in arranging numbers of objects in rows and then positioning the rows side-by-side in forming a two dimensional array of the objects where the objects being formed in the array are symmetric about their center vertical axes. Plastic blow molded bottles and other such containers that are symmetric about their center vertical axes are examples of such objects. In forming rows of desired numbers of symmetric objects, photoelectric sensors could be positioned adjacent the hold back gates of the infeed conveyor and before the openings of the slots between the pairs of row former arms, with the beams of the sensors directed perpendicularly across the infeed conveyor paths to count the number of objects conveyed from the infeed conveyor into each slot of the row former by each object breaking the beam.

However, difficulties were encountered in forming rows of objects when the shapes of the objects changed from the conventional shape, symmetrical about its center axis, to asymmetric shapes, for example a plastic, aluminum or cardboard container having a triangular cross section. Containers with necks such as bottles enable a photosensor beam to be passed between the necks of the bottles conveyed in front of the photosensor to generate signals used in counting the bottles conveyed past the sensor. Straight walled containers such as jars or aluminum cans provide a predictable curved surface at their sides that enable the use of proximity sensors in sensing the containers conveyed in front of the proximity sensors and providing signals for counting the containers conveyed past the sensors. However, for objects like containers having straight walls and irregular shaped cross sections such as triangular cross sections, a beam of a photosensor cannot pass between adjacent containers in a conveyed stream and a proximity sensor would provide different proximity signals depending on whether the sensor was sensing the smaller apex of a container or the larger side wall of a container passed by the sensor.

Figure 1:
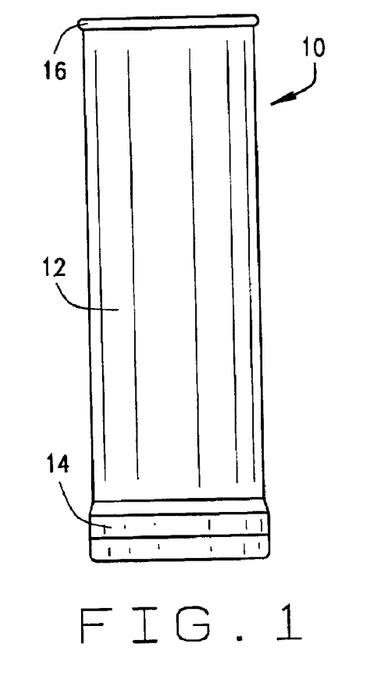
FIG. 1 is a side elevation view of a triangular cross section container of the type conveyed by the conveyor system of the invention.
Figure 2:
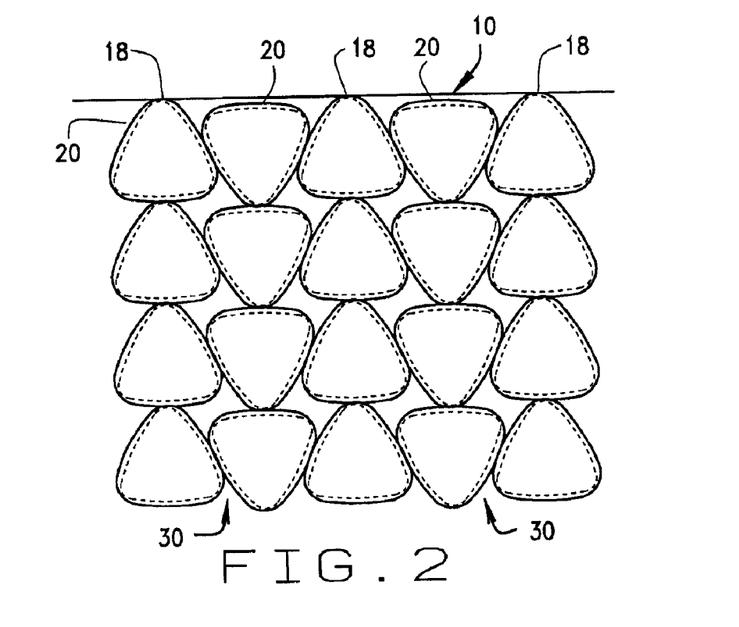
FIG. 2 is a schematic plan view of containers with triangular cross sections arranged in conveyed streams of the containers.

A side view of one example of a container 10 having a triangular cross section is shown in FIG. 1. The container 10 is basically comprised of a hollow triangular body 12 having an enlarged base 14 at its bottom and an enlarged rim 16 around a top opening of the container. Single file streams of these containers would be supplied by the infeed conveyor to the slots between the row former arms with the containers of each stream of containers positioned relative to each other as shown in FIG. 2. FIG. 2 is a schematic representation of the positions of the containers in four streams of containers supplied by the infeed conveyor to the four slots of a row former. As seen in FIG. 2, adjacent containers of each of the four rows of containers are rotated 180 degrees relative to each other to maximize the number of containers that can be arranged in each row of the row former. However, although the arrangements of the containers in each row shown in FIG. 2 maximize the number of containers occupying each row of the row former, problems arose in supplying desired numbers of the containers from the infeed conveyor into the slots of the row former.

Figure 3:
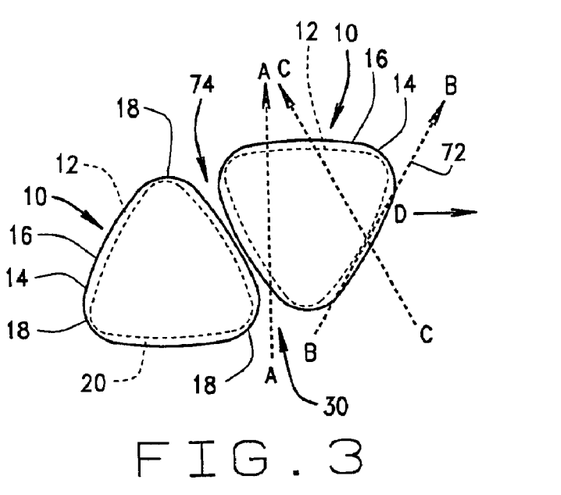
FIG. 3 is a schematic plan view of a pair of adjacent containers having triangular cross sections.

The triangular cross section shape of the containers presented the problem of how to count the number of containers supplied by the infeed conveyor to each row of containers formed in a row former slot. Prior art container counters employed photoelectric sensors that emit beams across the infeed conveyor at their hold back gates generally perpendicular to the direction of travel of containers passing through the infeed conveyor gates and entering into the row former slots. The overlapping arrangement of the triangular containers shown in FIG. 2 would prevent a beam of a prior art sensor from passing between two adjacent containers. Referring to FIG. 3, with two sequential containers 10 in a stream of containers being conveyed in the direction indicated by the arrow D, it can be seen that the prior art arrangement of positioning a photoelectric sensor to emit a beam, represented by the line A—A, across the stream of objects to count the numbers of objects conveyed will not work for containers having triangular shaped cross sections. As illustrated in FIG. 3, the overlapping arrangement of adjacent triangular shaped containers will prevent a beam directed perpendicularly across the conveyor path from passing between adjacent conveyors. Thus, changes were required from the prior art means of counting containers to determine the numbers of containers having triangular shaped cross sections that were supplied through the infeed conveyor gates to each row of the row former slots.

In addition, in using the arrangements of the containers shown in FIG. 2 in each conveyed path of the infeed conveyor supplying desired numbers of objects to the rows of the row former, problems arose when the rows of containers were moved by the row former from the infeed conveyor to the accumulating table surface of the conveyor system.

When the rows of containers arranged as shown in FIG. 2 were moved to the accumulating table surface and pushed across the table surface by subsequent rows of containers formed by the row former, the point contact between the apexes of containers in one row with the side walls of containers in the adjacent row would cause the containers to move away from their relative positions shown in FIG. 2. This was primarily due to the single point contact of the apex 18 of a container in one row pushing against the middle of a side wall 20 of a container in an adjacent row and the single point contact between the middle of a side wall 20 of a container in one row pushing against an apex 18 of a container in the adjacent row. The single point contact of the apex 18 with the side wall 20 would cause the container pushed by the adjacent container to tend to rotate or move to one side or the other of the apex as the containers are pushed across the accumulating table surface.

Figure 4:
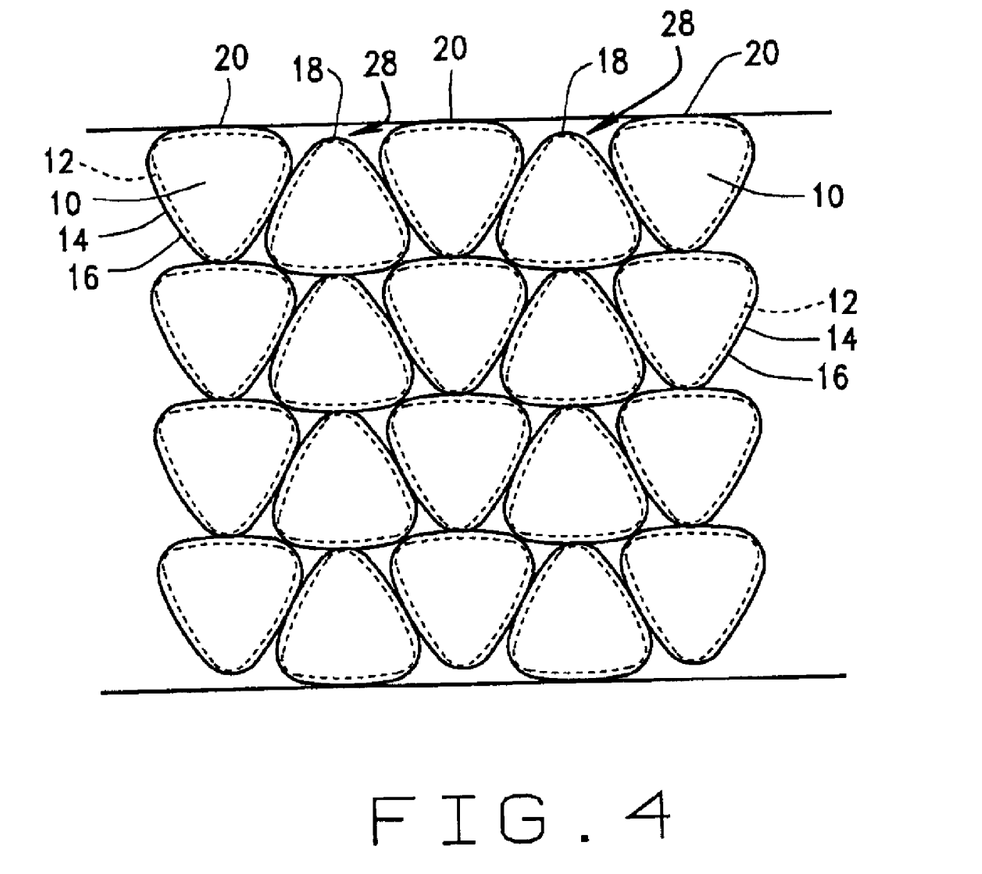
FIG. 4 is a schematic plan view of containers with triangular cross sections arranged in the staggered row arrangement of the invention.

To overcome the problem of movement of the triangular containers relative to each other as an array of the containers was pushed across the accumulating table surface by the row former, the inventor of the subject matter of the application created a novel arrangement of the triangular containers. In the novel arrangement of the containers, the containers are not arranged in an array of rows that extend straight across the two dimensional array with the side walls and apexes of adjacent containers in each row being positioned in a single vertical plane as shown in FIG. 2, but the containers of each row are arranged in a staggered arrangement shown in FIG. 4. The staggered arrangement of the containers shown in FIG. 4 provides a more stable two dimensional array of the containers than that of the array of FIG. 2. In the staggered array of FIG. 4, the side walls 20 of the containers in each row pushed by the apexes 18 of the containers in the adjacent row are also contacted at their opposite ends by the two containers on opposite sides of the container making apex contact. Also, the side wall 20 of each container in one row that pushes against an apex 18 of a container in an adjacent row also pushes against the two containers on opposite sides of the container with which it makes apex contact. Thus, the additional points of contact between the containers in adjacent rows prevents the containers being pushed from rotating to either side and provides a more stable two dimensional array of containers pushed across the accumulating table surface that maintains their relative positions as they are pushed across the accumulating table surface.

Figure 5:
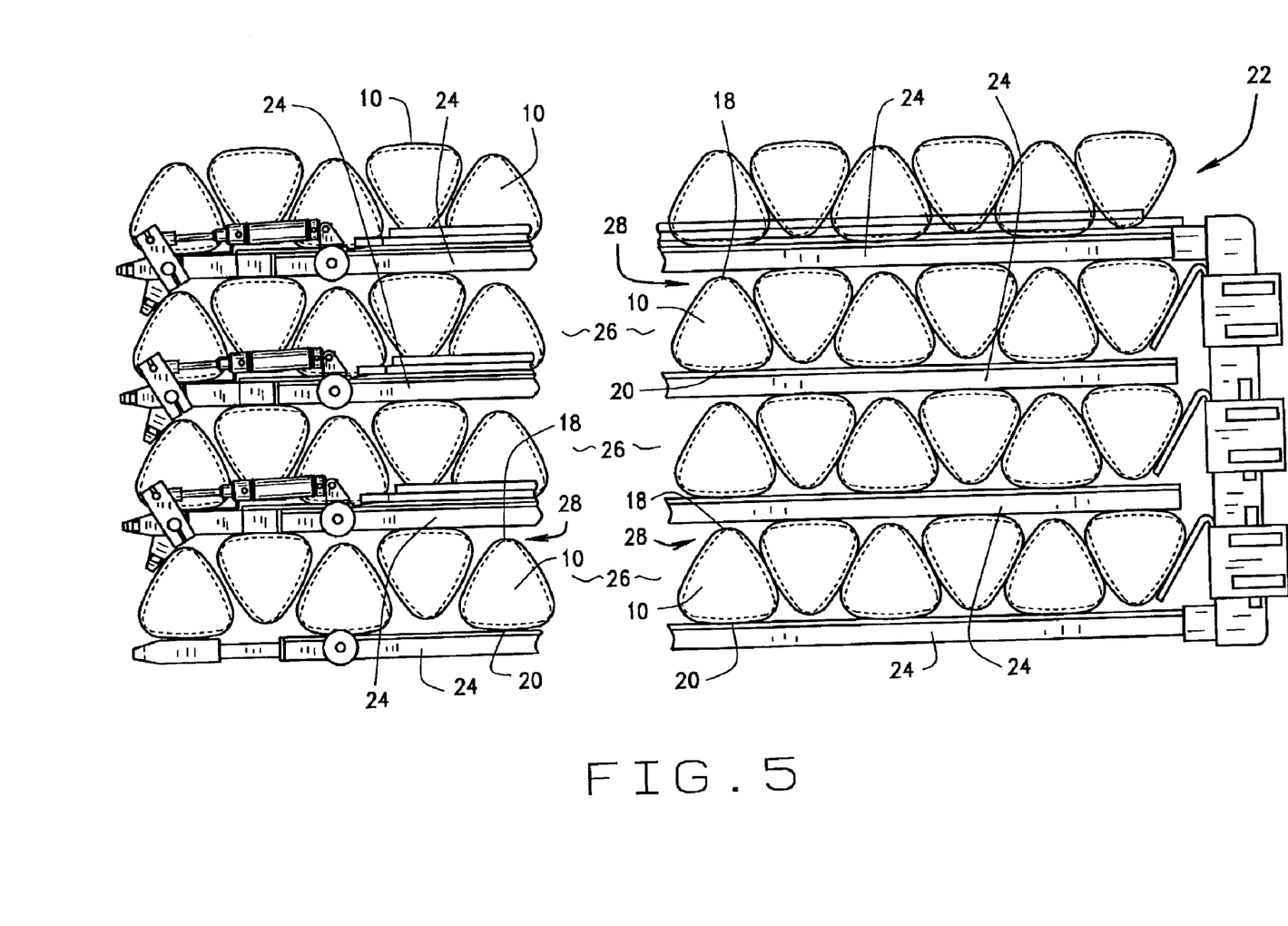
FIG. 5 is a plan view of the row former supplied with staggered rows of containers by the infeed conveyor of the invention.

However, the array arrangement shown in FIG. 3 presents the problem of how to establish the staggered relationship of the containers 10 in each row of the row former that will enable the row former to push staggered rows of containers arranged as shown in FIG. 4 onto the accumulating table surface. In order to provide a smooth transition from the infeed conveyor to the row former, guide rails on opposite sides of each conveyed path of the infeed conveyor must align with the pusher arms or pusher blades of the row former. However, to provide sufficient room between the pairs of opposed row former arms to enable the rows of containers formed between the arms to assume the staggered configuration of each row of containers shown in FIG. 4, the spacing between the opposed arms of the row former must be larger than a width dimension of the containers measured between the apex and opposite side wall of a container. FIG. 5 shows a row former 22 having pairs of pusher arms 24 or pusher blades that define the row former slots 26 between opposed pairs of arms. Opposed arms 24 are spaced from each other to create the staggered rows of the containers 10 shown in FIG. 4. With this spacing between the arms 24 of the row former 22, the side walls 20 of adjacent containers formed in rows between each pair of arms engage against one of the opposite arms and the apex 18 of each container is spaced by a predetermined gap 28 from the other arm, thereby creating the staggered configuration of the containers in the rows shown in FIG. 4. However, by spreading out the opposed pairs of arms of the row former to allow a gap 28 adjacent the apexes of the containers formed in rows between the arms, it would also be necessary to spread out the guide rails of each conveyed path of the infeed conveyor so that the infeed conveyor guide rails would also align with the pusher arms of the row former.

Moving the guide rails of the infeed conveyor further apart so that they align with the pusher arms of the row former would result in the infeed conveyor hold back gates mounted on one of the guide rails of each infeed conveyor path being moved by the distance of the gap 28 further away from the opposite infeed conveyor guide rail. Widening the space between the infeed conveyor guide rails would also enable the containers conveyed by the infeed conveyor to move from side to side as they are conveyed between the guide rails. This presented the problem of the possibility of containers passing by the hold back gate of the infeed conveyor when the gate has been moved to its closed position. This potential problem could not be overcome by increasing the length of the infeed conveyor hold back gate because the length of the gate must be short enough to enable the gate to pass into the cleft 30 formed between adjacent containers to close the gate quickly once the desired numbers of containers delivered by the infeed conveyor to the row former had passed the infeed conveyor sensors.

SUMMARY OF THE INVENTION

The infeed conveyor of the present invention overcomes the problems presented when conveying streams of objects having irregular shaped cross sections, for example triangular shaped cross sections, in counting numbers of objects conveyed and in supplying desired numbers of the containers from the conveyed paths of the infeed conveyor to the slots between the pusher arms of a row former.

To overcome the counting problem, each end of the infeed conveyor that supplies a stream of objects to the slots of the row former is provided with a photoelectric sensor that is oriented in a novel manner that enables it to count numbers of triangular shaped containers conveyed past the sensor from the infeed conveyor to the row former. In the first embodiment, a single photoelectric sensor associated with each conveyor path of the infeed conveyor is positioned so that a light beam emitted from a photoemitter of the sensor is directed at an oblique angle across the conveyor path to a photoreceptor of the sensor. The oblique angle is determined from the angles of the side walls 20 of the containers 10 conveyed by the infeed conveyor. Positioning the emitter so that its beam is emitted at the angle determined from the angular configuration of the containers enables the light beam emitted from the emitter to pass between pairs of adjacent containers to the receptor. This enables counting pairs of containers supplied to each row former slot to determine the numbers of containers supplied from the infeed conveyor to each slot. This embodiment of the counting sensors is employed where each slot of the row former is to be supplied with an even number of containers from the infeed conveyor.

In an alternative embodiment, where it is desired to count each individual container supplied from the infeed conveyor to each slot of the row former, pairs of photoelectric sensors, each including an emitter and receptor, are positioned on opposite sides of each conveyor path of the infeed conveyor. Each photoemitter of a pair is positioned so that it will emit a light beam that is directed at an oblique angle across the stream of objects supplied by the infeed conveyor to its associated receptor. Each of the photoelectric sensors is positioned so that their emitter light beams are emitted at an angle relative to the direction of the flow path of containers. By counting the times each beam of the two sensors is broken by pairs of adjacent containers supplied from the infeed conveyor through its hold back gate to the slot of the row former, a count of individual containers supplied to the slot of the row former is obtained.

In order to provide a smooth transition of the numbers of objects conveyed by the infeed conveyor through the hold back gates of the conveyor to the slots between the pusher arms of the row former, each conveyor path defined by pairs of guide rails of the infeed conveyor is provided with a restriction in the conveyor path on the guide rail opposite the guide rail on which the infeed conveyor hold back gate is mounted. This enables the guide rails of the infeed conveyor to be aligned with the pusher arms of the row former with the restrictions occupying the additional space in the conveyed paths of the infeed conveyor. The restrictions enable the gates of the infeed conveyor to be moved to their closed positions and hold back the streams of objects conveyed through the conveyed paths of the infeed conveyor in desired orientations of the containers, thus overcoming the potential problem of containers being conveyed past the closed hold back gates of the infeed conveyor due to the additional spacing between the infeed conveyor guide rails required by the additional spacing between the row former pusher arms. Depending on whether the infeed conveyor is supplying even or odd numbers of containers to the row former slots determines the relative positions of the restriction and gate on the opposite sides of the infeed conveyor paths.

With the modifications to the row forming conveyor system described above, the conveyor system of the invention is capable of obtaining accurate counts of containers having triangular shaped cross sections that are conveyed from the conveyed paths of the infeed conveyor to the slots of a row former and is capable of holding back the streams of containers conveyed along the conveyor paths of the infeed conveyor with the increased spacing between the opposed guide rails of the infeed conveyor being taken up by the restrictions.

BRIEF DESCRIPTION OF THE DRAWINGS

Further features of the invention are set forth in the following detailed description of the preferred embodiment of the invention and in the drawing figures wherein.

DETAILED DESCRIPTION OF THE PREFERRED EMBODIMENT

The infeed conveyor of the present invention is designed to overcome shortcomings experienced in prior art infeed conveyors in supplying desired numbers of irregular shaped objects, for example triangular cross section containers, to the slots between pairs of arms of a row former while maintaining a desired orientation between adjacent containers. More specifically, the infeed conveyor of the invention is designed to control a supply of triangular cross section containers to the slots of a row former providing a predetermined number of containers to each slot while maintaining a desired orientation of the containers supplied relative to each other. The infeed conveyor of the invention is an improvement over prior art infeed conveyors and therefore includes many component parts and/or features of prior art infeed conveyors to which the novel components of the invention have been added to achieve the desired operation of the infeed conveyor. Because the infeed conveyor of the invention employs many component parts of prior art conveyors, those parts will only be described generally to simplify the description of the invention.

Figure 6:
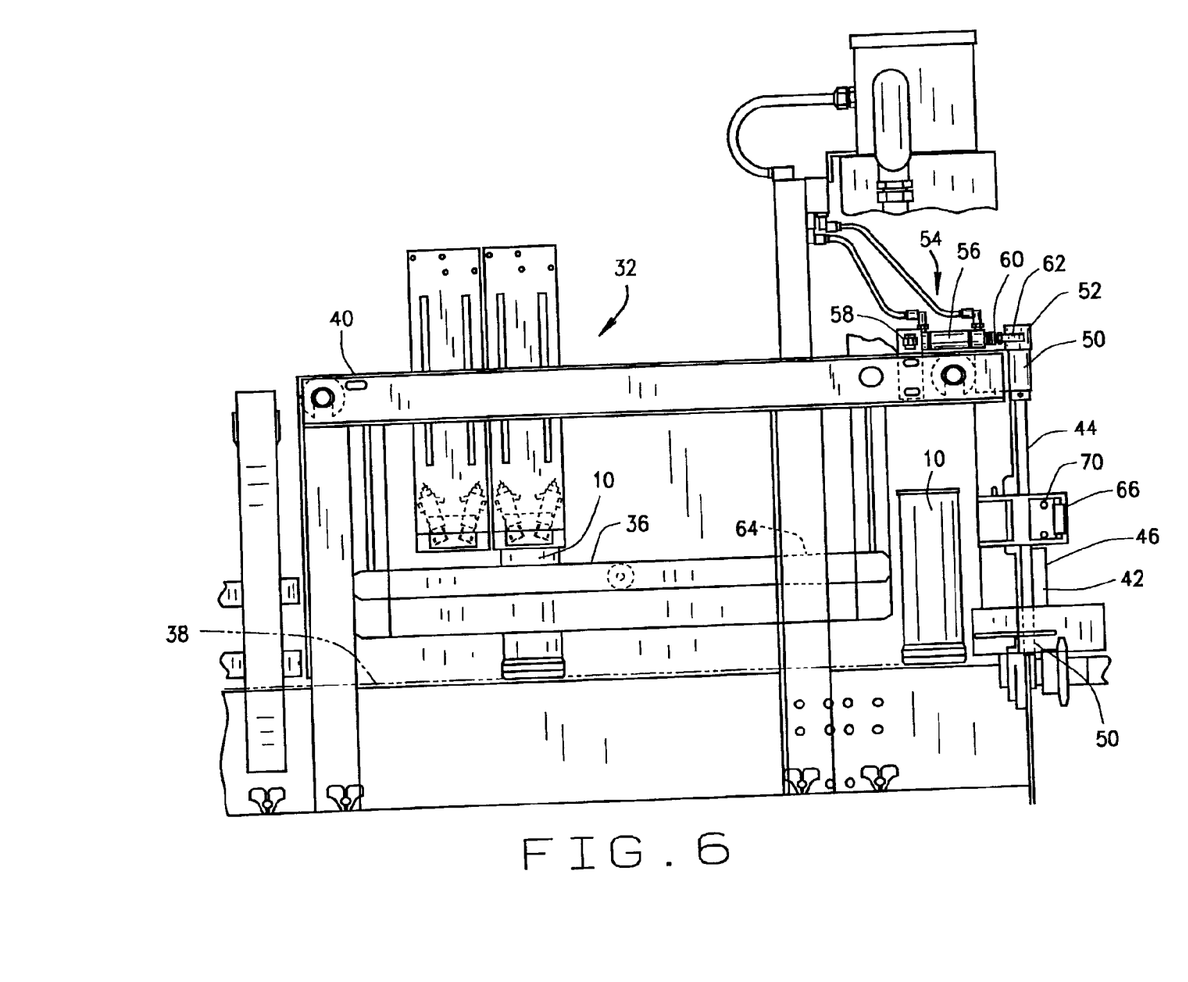
FIG. 6 is a side elevation view of the outlet of the infeed conveyor of the invention.
Figure 7:
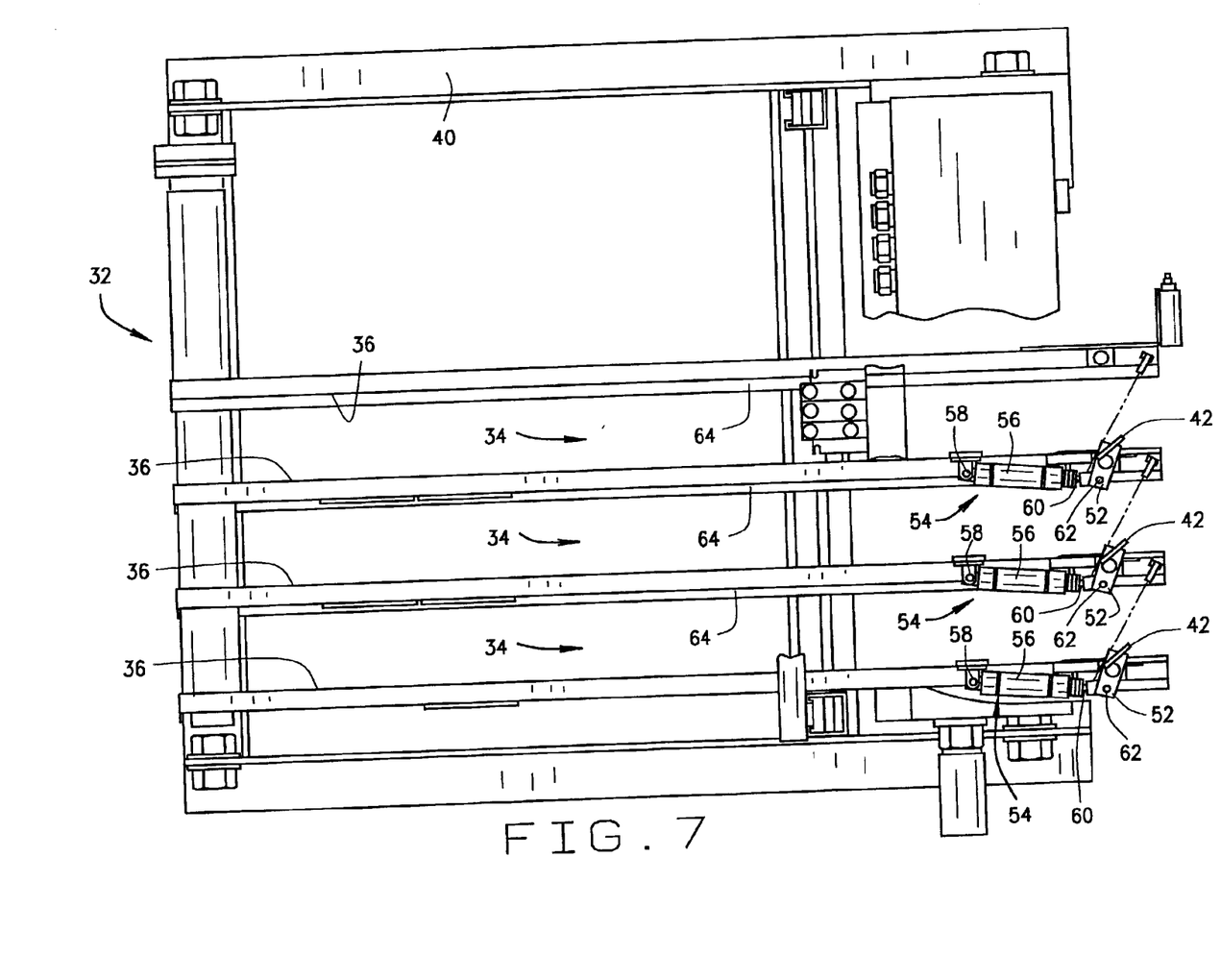
FIG. 7 is a plan view of the infeed conveyor.
Figure 8:
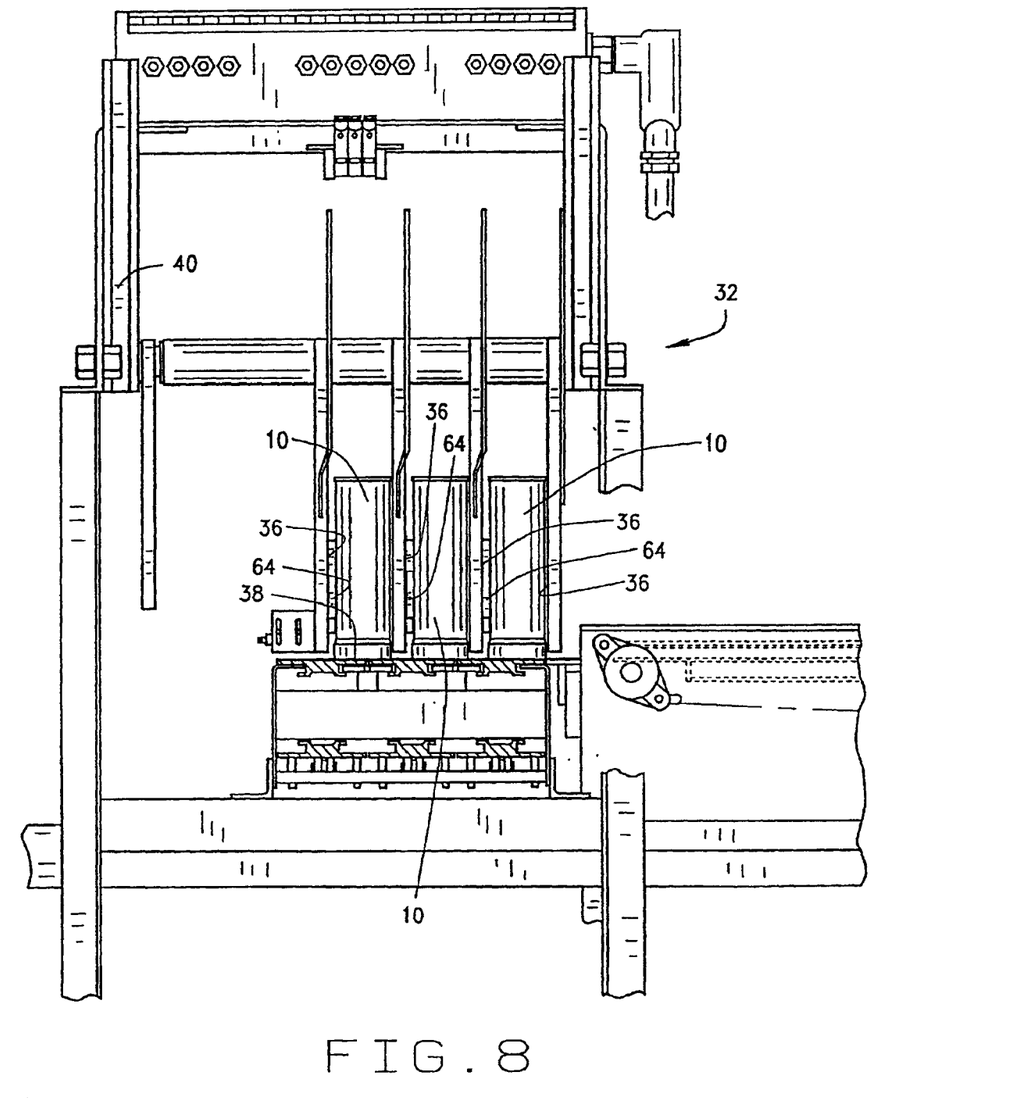
FIG. 8 is an end elevation view of the infeed conveyor.

A partial side elevation view of the outlet portion of an infeed conveyor incorporating the improvements of the invention is shown in FIG. 6. The outlet portion of the conveyor 32 receives streams of conveyed objects, in this example triangular cross section containers 10, from the left as viewed in FIG. 6 and holds back the stream of objects and selectively supplies desired numbers of the objects to the slots of a row former (not shown) that is positioned to the right of the outlet portion 32 of the infeed conveyor as viewed in FIG. 6. FIG. 7 is a top plan view of the outlet portion of the conveyor 32 shown in FIG. 6 and FIG. 8 is an end elevation view of the conveyor from the right of the outlet portion of the conveyor as shown in FIG. 6. In the example shown, the infeed conveyor has three channels or conveyor paths 34 defined by pairs of guide rails 36 that direct streams of the containers 10 to the row former (not shown). However, the features of the invention to be described may be employed in conveyor systems channeling fewer than three streams of containers along conveyor paths or more than three streams of containers along conveyor paths.

As best seen in FIGS. 6 and 8, the outlet portion of the infeed conveyor 32 is positioned above a conveying surface 38 that conveys streams of the containers 10 through the outlet portion and to the row former (not shown). As seen in FIG. 8, the conveying surface 38 is provided by three separate continuous belt conveyors that extend beneath the infeed conveyor 32 and beneath the row former (not shown). In operation, the conveying surface 38 defined by the three belt conveyors runs continuously beneath the infeed conveyor 32 providing a continuous stream of conveyed containers 10 in the three conveyor paths 34 of the conveyor. The operation of the infeed conveyor 32 controls the supply of containers 10 to the row former and also controls the numbers of containers supplied.

The infeed conveyor includes a framework 40 that extends over the conveying surface 38 of the belt conveyors. The framework 40 supports the four panels or guide rails 36 that extend downwardly from the framework to positions over the conveying surface 38. The four guide rails 36 define the three channels or conveyor paths 34 of the conveyor that each receive streams of the containers 10 conveyed to the infeed conveyor 32 from the upstream portion of the conveyor system (not shown) to the left of FIGS. 6 and 7. The objects in the streams of objects supplied to the conveyor paths 34 between the opposed rails 36 are arranged in alternating orientations as shown in FIG. 2.

To hold back the streams of conveyed containers 10 on the conveying surface 38 until they are needed to fill the slots of a row former, each conveyor path 34 of the infeed conveyor 32 is provided with a gate 42. Each gate 42 is basically a rectangular plate mounted to a vertical shaft 44 of an actuator mechanism. The gate 42 is mounted to an intermediate portion of the shaft 44 so that the gate will engage with an intermediate portion of a container 10 conveyed on the conveying surface 38 between the base 14 and rim 16 of the container when the gate is closed as will be explained. The gate 42 projects a short distance outwardly from the shaft 44 to a distal edge 46 of the gate. The shaft 44 is supported by the framework 40 to rotate about a center axis of the shaft. Opposite ends of the shaft 44 pass through bearing blocks 50 that hold the shaft in its vertical orientation. A crank arm 52 is secured to the top end of the shaft 44 just above the uppermost bearing block 50.

A two position pneumatic actuator 54 is connected between the crank arm 52 and the framework 40 for each gate shaft 44. As best seen in FIGS. 6 and 7, a cylinder 56 of the actuator 54 has one end secured by a pivoting connection 58 to the framework 40. A piston rod 60 projects from the opposite end of the actuator cylinder 56 and is connected by a pivoting connection 62 to the crank arm 52. Selective supply of pneumatic pressure to opposite ends of the actuator cylinder 56 causes the actuator rod 60 to reciprocate between a first, extended position of the rod relative to the cylinder and a second, retracted position of the rod relative to the cylinder. By the pivoting connection 62 of the rod 60 with the crank arm 52, the controlled movement of the actuator rod 60 between its first and second positions causes the gate shaft 44 to rotate between first and second positions which in turn causes the gate 42 to move to its first, closed position shown in FIGS. 7 and 9 and its second, opened position shown in dashed lines in FIG. 9. In its opened position, the gate 42 projects in a direction from the shaft 44 that is generally parallel with the direction D of the containers conveyed through the conveyed path 34. In its closed position shown in FIG. 9, the gate 42 projects at an oblique angle relative to the direction D into the conveyed path 34. In the closed position of the gate shown in FIG. 9, it will engage against a portion of the side wall 20 of a container conveyed by the conveying surface 38 through the conveyor path 34 and hold back the container 10 in the path.

As explained earlier, in order to provide a smooth transition of the numbers of containers conveyed by the infeed conveyor 32 through the hold back gates 42 to the slots 26 of the row former 22 of FIG. 5, the guide rails 36 of the infeed conveyor are spaced apart so that they will align with the row former arms or pusher arms 24 of the row former. However, this increased spacing between the guide rails 36 of the infeed conveyor presents the potential problem of containers 10 conveyed by the conveyor engaging with the gate 42 that has been moved to its closed position shown in FIGS. 7 and 9 and potentially rotating or moving around the gate distal edge 46 past the closed hold back gate 42 due to the additional lateral spacing or width between the guide rails 36 of the conveyor. To prevent this from happening, each conveyor path 34 of the infeed conveyor is provided with a restriction 64 in the form of an elongate panel that is secured to one of the guide rails 36 of each conveyed path of the infeed conveyor. As seen in FIG. 7, the elongate panel restriction 64 is secured to a side of a guide rail 36 of each opposed pair of guide rails opposite the gate 42 of the conveyor path 34 defined between the pair of guide rails. The elongate panel restriction 64 extends along the entire length of the outlet portion of the infeed conveyor 32 shown in FIG. 7, extending even slightly beyond the hold back gate 42 of the conveyor path. As seen in FIG. 8, each restriction panel 64 has a vertical height and is vertically positioned on the guide rail 36 so that it will engage with containers 10 conveyed through the infeed conveyor against an intermediate portion of the container body 12 between the base 14 and the rim 16. Each restriction panel 64 has a thickness dimension that is equal to the dimension of the gap 28 created between the apexes 18 and opposite pusher arms 24 of the staggered rows of containers formed in the row former 22 shown in FIG. 5. Thus, by providing the elongate restriction panels 64 in the conveyor paths 34 of the infeed conveyor 32, the panels take up the additional spacing between the infeed conveyor guide rails 36 needed to align the guide rails with the pusher arms 24 of the row former and prevent excessive side-to-side movement of containers 10 conveyed by the infeed conveyor along the conveyor paths 34 that could potentially result in one or more of the containers moving past the hold back gates 42 or becoming disoriented from the arrangement of FIG. 2 when the gates have been moved to their closed positions.

By providing the restriction panel 64 opposite each gate 42 of the infeed conveyor as shown in FIG. 7, the engagement of the gate against the side wall 20 of the end container 10 of a conveyed stream of containers will hold the container in its orientation shown in FIG. 2 and thereby hold subsequent containers of the conveyed stream of containers in their desired relative positions shown in FIG. 2.

Figure 9:
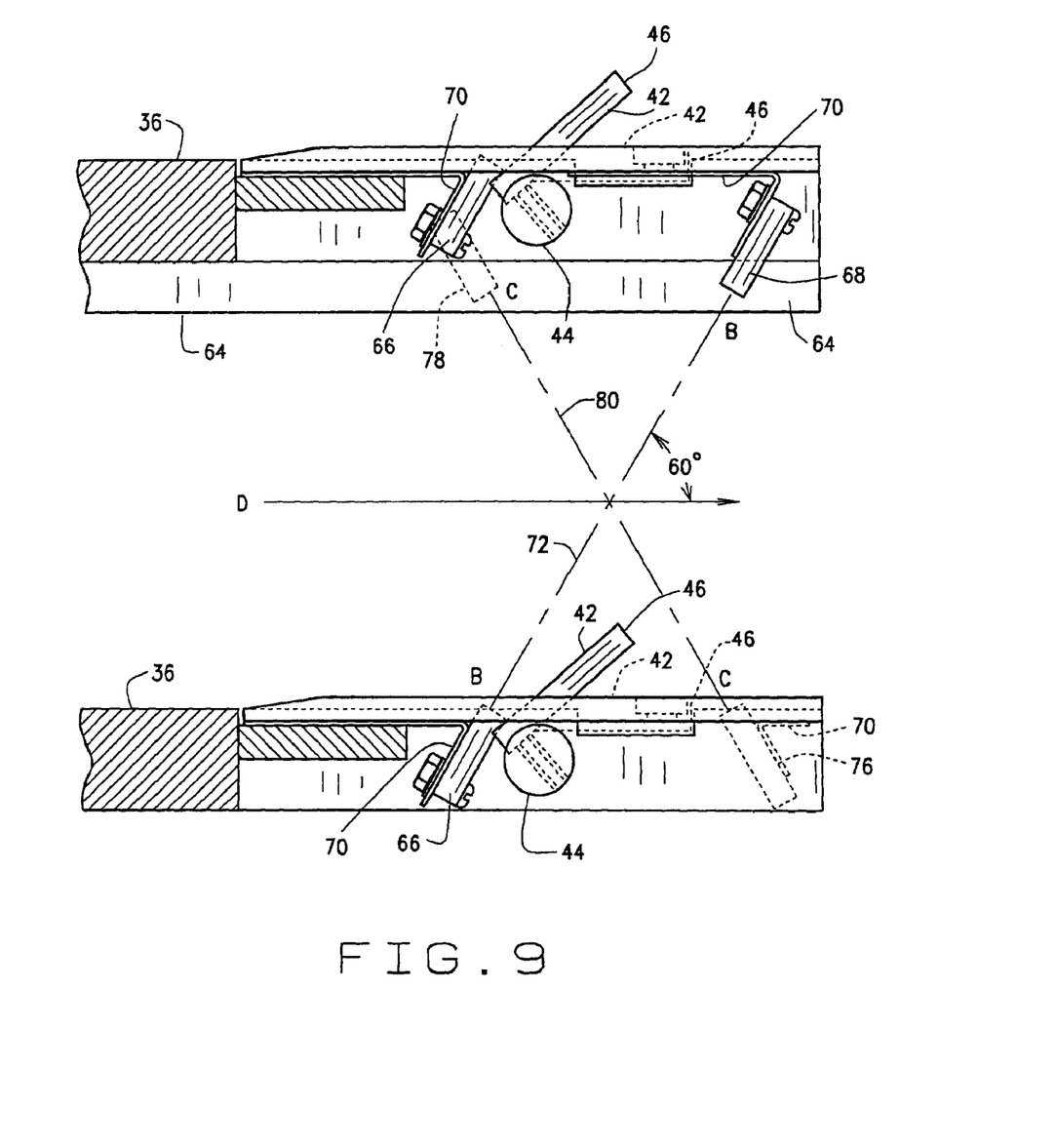
FIG. 9 is a partial plan view of the infeed conveyor showing the positions of photoelectric sensors and the restriction employed on the conveyor.

Also positioned on opposite guide rails 36 of each conveyor path 34 of the infeed conveyor are photoelectric sensors comprised of pairs of light beam emitters 66 and light beam receptors 68. The preferred photoelectric sensors are optic fiber light emitters and their associated optic fiber receptors of the type manufactured by Banner Engineering Corp. of Minneapolis, Minn. The emitters 66 and receptors 68 are mounted to the guide rails 36 of each opposite pair of rails by brackets 70 that are bent at an angle. As best seen in FIG. 9, each of the brackets 70 positions the photoemitter 66 and photoreceptor 68 so that a light beam 72 emitted from the emitter 66 is directed at an oblique angle relative to the direction D of containers conveyed through the conveyor path 34 of the infeed conveyor. In the preferred embodiment, with the containers 10 having triangular cross sections that are equilateral triangles, the oblique angle between the direction in which a beam of light 72 is emitted from the emitter 66 toward the receptor 68 and the conveyed path direction D of the containers through the conveyor path 34 of the infeed conveyor is a 60 degree angle represented by the line B—B of FIGS. 3 and 9. With this orientation of the emitter 66 and the receptor 68 on opposite sides of the conveyed path 34, a light beam will pass through the space 74 between the opposed side walls 20 of adjacent containers 10 which is oriented in the same angle as the light beam. With each light beam emitted by the emitter 66 passing between pairs of adjacent containers 10 and being sensed by the opposite receptor 68, the orientation of the light beam emitter 66 and light beam receptor 68 of the invention can provide signals used to count pairs of containers having triangular shaped cross sections passed between the sensors and thereby provide an accurate number of the containers conveyed by the infeed conveyor 32 through the hold back gates 42 to the row former (not shown) for even numbers of containers supplied to the rows of the row former. The light beam emitted by the emitter 66 and sensed by the receptor 68 is also used to control the closing of the gate 42 to ensure that the gate will quickly close when the desired number of containers has passed the gate.

To provide counting the numbers of individual containers supplied by the infeed conveyor 32 to the slots of the row former, an additional photosensor is added comprising an additional photoemitter 76 and photoreceptor 78 positioned on the opposite guide rails 36 of each of the conveyor paths 34. The additional photoemitter and photoreceptor are positioned so that the beam of light 80 emitted from the second emitter 76 is oriented at an angle relative to the beam of light 72 emitted by the first photoemitter 66 which enables counting individual numbers of containers passed through the two beams of light by counting the times both beams of light pass between the containers. The two beams of lights crossing in the conveyor path 34 will each pass between pairs of containers where the spacings between the opposed side walls of adjacent containers are oriented in one of the two vertical planes in which the two beams of light are also contained. Thus, by adding the signals obtained from each of the pairs of photosensors arranged on opposite sides of the conveyor path 34, numbers of individual containers that pass through the beams of light can be determined.

With the improvements to the infeed conveyor provided by the gate restriction and sensors of the invention described above, the improved infeed conveyor can control the supply of containers having triangular cross sections to a row former while maintaining a desired orientation of adjacent containers supplied to the row former and sensing the numbers of containers conveyed through the infeed conveyor gates to the row former.

While the present invention has been described by reference to a specific embodiment, it should be understood that modifications and variations of the invention may be constructed without departing form the scope of the invention defined in the following claims.

What is claimed:

1. An apparatus for sensing conveyed objects, the apparatus comprising:

a conveyor for conveying objects in a first direction along a conveyed path;

a pair of arms on opposite sides of the conveyed path, the pair of arms being movable together across the conveyed path;

a photosensor positioned adjacent the conveyor to emit a beam of light from the photosensor in a second direction across the conveyed path, the second direction being oriented at an oblique angle relative to the first direction; and, a gate positioned adjacent the conveyor, the gate being moveable between first and second positions relative to the conveyor where in the first position the gate is oriented in alignment with the first direction along the conveyed path and in the second position the gate is oriented at an angle relative to the first direction.

2. The apparatus of claim 1, wherein:

the conveyor is configured for conveying objects in a single file line.

3. The apparatus of claim 2, wherein:

the conveyor is configured for conveying objects that have a triangular cross-section.

4. The apparatus of claim 1, wherein:

the oblique angle is substantially a 60 degree angle.

5. The apparatus of claim 1, wherein:

the photosensor is one of a pair of photosensors that are each positioned adjacent the conveyor to emit a beam of light across the conveyed path with a first of the photosensors emitting the beam of light in the second direction and a second of the photosensors emitting a beam of light in a third direction, the third direction being oriented at an oblique angle relative to the first direction.

6. The apparatus of claim 1, wherein:

the conveyor has a conveying surface that supports the objects conveyed along the conveyed path.

7. The apparatus of claim 6, wherein:

a pair of parallel rails extend along the conveyed path on opposite sides of the conveying surface.

8. The apparatus of claim 7, wherein:

the photosensor is mounted on one of the rails.

9. An apparatus for sensing conveyed objects, the apparatus comprising:
- a conveyor for conveying objects in a first direction along a conveyed path;
- a photosensor positioned adjacent the conveyor to emit a beam of light from the photosensor in a second direction across the conveyed path, the second direction being oriented at an oblique angle relative to the first direction;
- the photosensor is one of a pair of photosensors that are each positioned adjacent the conveyor to emit a beam of light across the conveyed path with a first of the photosensors emitting the beam of light in the second direction and a second of the photosensors emitting a beam of light in a third direction, the third direction being oriented at an oblique angle relative to the first direction; and
- the first and second photosensors are positioned where the second direction and third direction are oriented at an oblique angle with respect to one another.

10. The apparatus of claim 9, wherein:
the oblique angle is substantially a 60 degree angle.

11. An apparatus for sensing conveyed objects, the apparatus comprising:
- a conveyor for conveying objects in a first direction along a conveyed path;
- a photosensor positioned adjacent the conveyor to emit a beam of light from the photosensor in a second direction across the conveyed path, the second direction being oriented at an oblique angle relative to the first direction;
- a gate is positioned adjacent the conveyed path and is moveable between first and second positions relative to the conveyor where in the first position the gate is oriented parallel with the first direction and in the second position the gate is oriented at an angle relative to the first direction; and
- a restriction is positioned adjacent the conveyed path on an opposite side of the conveyed path from the gate.

12. The apparatus of claim 11, wherein:
the restriction is an elongate panel that extends over the conveyed path.

13. The apparatus of claim 11, wherein:
the conveyor is configured for conveying objects in a single file line.

14. The apparatus of claim 13, wherein:
the conveyor is configured for conveying objects that have a triangular cross-section.

15. The apparatus of claim 11, wherein:
the photosensor is one of a pair of photosensors that are each positioned adjacent the conveyor to emit a beam of light across the conveyed path with a first of the photosensors emitting the beam of light in the second direction and a second of the photosensors emitting a beam of light in a third direction, the third direction being oriented at an oblique angle relative to the first direction.

16. The apparatus of claim 15, wherein:
the first and second photosensors are positioned where the second direction and third direction are oriented at an oblique angle.

17. The apparatus of claim 16, wherein:
the oblique angle is substantially a 60 degree angle.

18. The apparatus of claim 11, wherein:
the conveyor has a conveying surface that supports the objects conveyed along the conveyed path.

19. The apparatus of claim 18, wherein:
a pair of parallel rails extend along the conveyed path on opposite sides of the conveying surface.

20. The apparatus of claim 19, wherein:
the photosensor is mounted on one of the rails.

21. The apparatus of claim 11, wherein:
- a pair of guide rails extend along opposite sides of the conveyed path, the restriction is connected to one of the guide rails giving the conveyed path a reduced width; and,
- a row former is positioned adjacent the infeed conveyor, the row former has pusher arms that are aligned with the infeed conveyor guide rails and the pusher arms have a width between an opposed pair of pusher arms that is larger than the reduced width of the conveyed path.

22. A method of sensing conveyed objects having a triangular cross-section, the method comprising:
- conveying the objects in a single file line in a first direction with at least some of the objects abutting each other;
- positioning a first photosensor adjacent the conveyed line of objects to emit a beam of light from the first photosensor in a second direction that is oriented at an oblique angle relative to the first direction;
- positioning a second photosensor adjacent the conveyed line of objects to emit a beam of light from the second photosensor in a third direction that is oriented at an oblique angle relative to the first direction; and,
- positioning the first photosensor and the second photosensor where the second and third directions are oriented at an oblique angle to each other.

23. The method of claim 22, further comprising:
positioning the photosensor where the oblique angle is substantially a 60 degree angle.

24. The method of claim 22, further comprising:
conveying the objects on a conveying surface between a pair of parallel rails extending along opposite sides of the conveying surface.

* * * * *